United States Patent
Ujhazy et al.

(10) Patent No.: US 9,050,024 B2
(45) Date of Patent: Jun. 9, 2015

(54) METHOD AND APPARATUS FOR DETECTION AND TREATMENT OF RESPIRATORY DISORDER BY IMPLANTABLE DEVICE

(75) Inventors: Anthony John Ujhazy, East Lindfield (AU); Gregory Newton Brewer, Croydon (AU)

(73) Assignee: RedMed Limited (AU)

( * ) Notice: Subject to any disclaimer, the term of this patent is extended or adjusted under 35 U.S.C. 154(b) by 580 days.

(21) Appl. No.: 12/712,856

(22) Filed: Feb. 25, 2010

(65) Prior Publication Data

US 2010/0152553 A1    Jun. 17, 2010

Related U.S. Application Data

(63) Continuation of application No. 10/598,136, filed as application No. PCT/AU2005/000255 on Feb. 21, 2005, now Pat. No. 7,697,990.

(60) Provisional application No. 60/546,551, filed on Feb. 20, 2004.

(51) Int. Cl.
    *A61N 1/36*     (2006.01)
    *A61B 5/08*     (2006.01)
    *A61B 5/053*    (2006.01)
    *A61B 5/00*     (2006.01)
    *A61N 1/08*     (2006.01)

(52) U.S. Cl.
    CPC .............. *A61B 5/0809* (2013.01); *A61B 5/0538* (2013.01); *A61B 5/4818* (2013.01); *A61N 1/08* (2013.01); *A61N 1/3601* (2013.01)

(58) Field of Classification Search
    CPC .... A61B 7/003; A61B 7/4818; A61B 5/4818; A61N 1/3601; A61N 1/36114
    USPC ..................... 607/42; 600/529–543
    See application file for complete search history.

(56) References Cited

U.S. PATENT DOCUMENTS

| 3,608,543 A | * | 9/1971 | Longini et al. .............. 600/536 |
| 4,830,008 A | | 5/1989 | Meer |
| 4,944,310 A | | 7/1990 | Sullivan |

(Continued)

FOREIGN PATENT DOCUMENTS

| EP | 0507580 | 7/1996 |
| EP | 0702977 | 3/2003 |

(Continued)

OTHER PUBLICATIONS

Tompsett, Ralph. "Cheyne-Stokes Respiration." Encyclopedia Americana. 2008. Grolier Online. Jan. 4, 2008 <http://ea.grolier.com/cgi-bin/article?assetid=0090330-00>.

(Continued)

*Primary Examiner* — Paula J Stice

(74) *Attorney, Agent, or Firm* — Lerner, David, Littenberg, Krumholz & Mentlik, LLP

(57) ABSTRACT

Methods and apparatus for detection and treatment of respiratory disorders using implanted devices are described. In one form, afferent nerves are electrically or electro-mechanically stimulated to increase the tone of upper airway muscles. Detection of respiratory disorders is carried out using electrodes implanted in sub-pectoral regions. Open and closed airway apneas are distinguished using a combination of acoustic detectors and electrical transducers.

32 Claims, 1 Drawing Sheet

(56) References Cited

U.S. PATENT DOCUMENTS

| | | | |
|---|---|---|---|
| 5,158,080 A | 10/1992 | Kallok | |
| 5,178,156 A | 1/1993 | Takishima et al. | |
| 5,207,230 A | 5/1993 | Bowers | |
| 5,385,144 A * | 1/1995 | Yamanishi et al. | 600/330 |
| 5,540,733 A | 7/1996 | Testerman et al. | |
| 6,029,665 A | 2/2000 | Berthon-Jones | |
| 6,076,015 A | 6/2000 | Hartley et al. | |
| 6,240,316 B1 | 5/2001 | Richmond et al. | |
| 6,251,126 B1 | 6/2001 | Ottenhoff et al. | |
| 6,409,675 B1 * | 6/2002 | Turcott | 600/508 |
| 6,445,942 B1 | 9/2002 | Berthon-Jones et al. | |
| 6,636,767 B1 | 10/2003 | Knudson et al. | |
| 6,675,797 B1 | 1/2004 | Berthon-Jones | |
| 6,904,320 B2 | 6/2005 | Park et al. | |
| 2002/0049479 A1 | 4/2002 | Pitts | |
| 2004/0002742 A1 | 1/2004 | Florio | |
| 2004/0102712 A1 | 5/2004 | Belacazar et al. | |
| 2004/0111040 A1 | 6/2004 | Ni et al. | |
| 2004/0186526 A1 | 9/2004 | Freeberg | |
| 2005/0004610 A1 | 1/2005 | Kim et al. | |
| 2005/0039745 A1 | 2/2005 | Stahmann et al. | |
| 2005/0043644 A1 | 2/2005 | Stahmann et al. | |

FOREIGN PATENT DOCUMENTS

| | | |
|---|---|---|
| WO | 9215364 | 9/1992 |
| WO | 9221407 | 12/1992 |

OTHER PUBLICATIONS

Hill, Richard W. "Respiration." Encyclopedia Americana. 2008. Grolier Online. Jan. 4, 2008 <http://ea.grolier.com/cgibin/ article?assetid=0331290-001.

Merriam-Webster Online Dictionary Jan. 4, 2008 <http://m-w.com/dictionary/afferent>.

International Search Report and Written Opinion for Application No. PCT/AU2005/000225 dated Apr. 13, 2005.

* cited by examiner

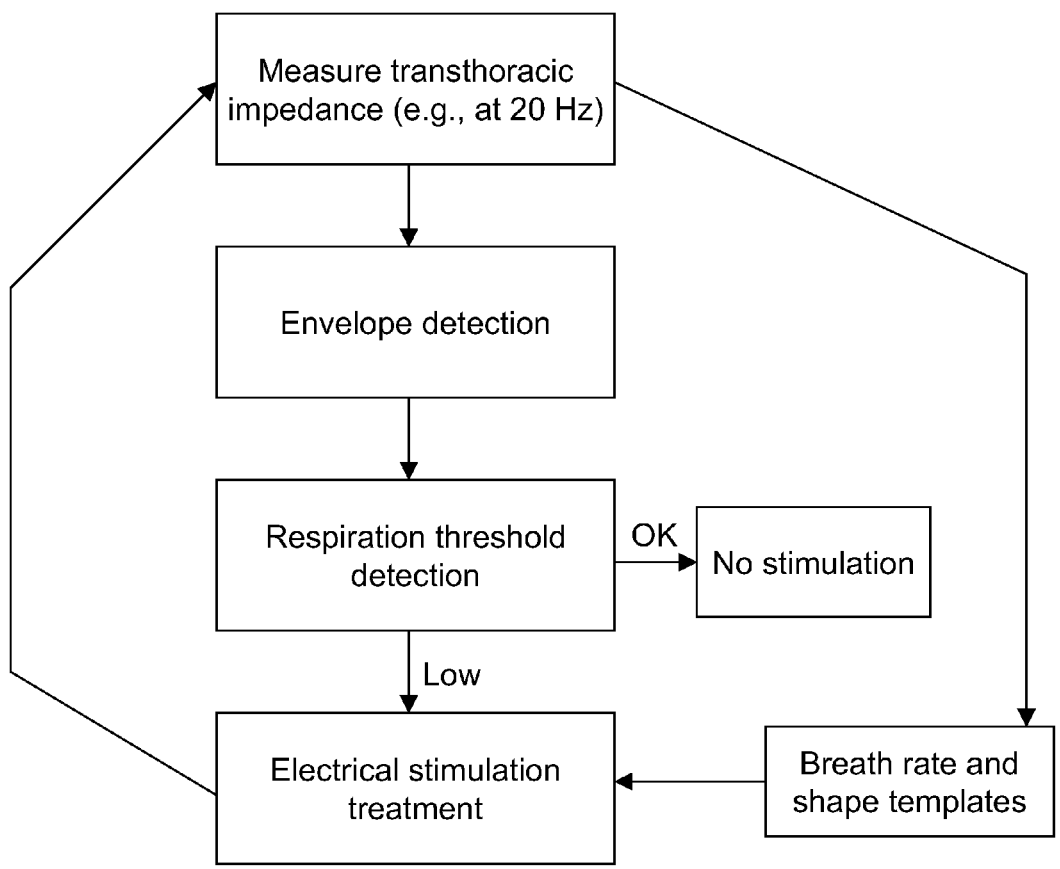

METHOD AND APPARATUS FOR DETECTION AND TREATMENT OF RESPIRATORY DISORDER BY IMPLANTABLE DEVICE

The present application is a continuation of U.S. application Ser. No. 10/598,136 which is a §371 application of PCT/AU05/00255 filed Feb. 21, 2005, now issued as U.S. Pat. No. 7,697,990, which claims priority to U.S. Provisional patent application 60/546,551 filed Feb. 20, 2004.

1.0 FIELD OF THE INVENTION

The invention relates to the detection and treatment of respiratory disorders by implantable electrical and/or electromechanical devices.

2.0 BACKGROUND

Nasal CPAP treatment of sleep Disordered Breathing (SDB), for example as taught by Sullivan in U.S. Pat. No. 4,944,310 has become the standard. However, other techniques are known. Uvulopalatopharyngoplasty (UPPP) is a surgical procedure for the treatment of severe Obstructive Sleep Apnea (OSA). In UPPP, soft tissue on the back of the throat and soft palate (the uvula) is removed. Oral Mandibular Advancement Devices are dental appliances used to treat patients with Obstructive Sleep Apnea (OSA) and Upper Airway Resistance Syndrome (UARS). They look similar to mouth guards used in sports. Other techniques involve electrical stimulation.

U.S. Pat. No. 6,636,767 describes how an electrode is placed in stimulating contact with an airway passage-controlling muscle of the patient. The electrode is energized to contract the muscle and alter the airway passage.

However some researchers have noted (Guilleminault et al. Chest 1995 107:67-73) that "The results obtained by us and others do not, at this time, give convincing support for the use of electrical stimulation using submental surface or intraoral electrodes as a viable approach for effective control of obstructive sleep apnea syndrome symptoms."

It is known that central apnea and obstructive apnea can be discriminated by flow and effort sensors. See for example U.S. Pat. Nos. 6,675,797; 6,029,665; and 6,445,942.

It is an object of the invention to provide improved detection and treatment of respiratory disorders using implanted devices.

3.0 SUMMARY OF THE INVENTION

In accordance with a first aspect of the invention, treatment of a respiratory disorder utilises afferent nerve stimulation.

In accordance with a second aspect of the invention, treatment of a respiratory disorder utilises efferent nerve stimulation.

In accordance with another aspect of the invention, upper airway muscle tone is indirectly stimulated.

In accordance with another aspect of the invention, baseline treatment is initiated when the patient is asleep in order to achieve an increased background tone of upper airway muscles to prevent airway collapse.

In accordance with another aspect of the invention, treatment is initiated or increased above baseline treatment when obstructive sleep apnea is detected.

In accordance with another aspect of the invention, respiratory disorders are detected with the use of an implanted device.

In accordance with another aspect of the invention, open and closed airway (also called, central and obstructive) apneic events are distinguished by a combination of implanted electrodes and acoustic transducers.

4.0 BRIEF DESCRIPTION OF THE DRAWING

FIG. 1 shows method for detection and treatment of respiratory disorders using implantable devices.

5.0 DETAILED DESCRIPTION OF PREFERRED EMBODIMENTS

5.1 Treatment

For treatment of detected Obstructive Sleep Apnea (OSA), one method is electrical stimulation of afferent nerves, the objective of which is to indirectly cause an increase of the tone of upper airway muscles normally involved with maintenance of upper airway patency. In OSA, it is known that tone of these upper airway muscles typically decreases, contributing to a collapse and obstruction of the airway. Typically during wakefulness in patients with OSA, reflexes work to maintain tone in upper airway muscles thereby preventing airway collapse. The object of the present method is to substitute or enhance this reflex mechanism during sleep, thereby restoring or maintaining airway patency. The site of electrical stimulation is within or adjacent to the genioglossus muscle or in the vicinity of the hypoglossal motor nucleus or excitatory afferent nerve pathways leading to this structure. The amplitude, frequency and pulse width of electrical stimulation is controlled such that sufficient stimulation of afferent nerves is achieved without significant stimulation of efferent nerves, and without eliciting arousal from sleep. This stimulation of afferent nerves thus influences the patient's own intrinsic control system which modulates upper airway tone. The electrical simulation of afferent nerves typically consists of trains of electrical pulses, for example; 0.1 mA amplitude, 0.1 ms duration, train length of 10-30 pulses repeated every 1 minute. This level is defined as 1 unit of stimulation.

A second method for stimulation of afferent nerves is by using mechanical stimulation. A mechanical element, for example a piezo-electric element, is implanted at a site in the vicinity of the upper airway, for example, within or adjacent to the base of the genioglossus muscle. The element is electrically connected to the controller of the implanted device. The controller elicits vibration of the mechanical element by sending an electrical signal. Vibration of the element elicits stimulation of mechanoreceptor afferent nerve endings within the upper airway. Stimulation of these mechanoreceptors provides an excitatory input into the patient's intrinsic control system of the upper airway, thereby increasing tone of upper airway muscles and hence restoring or maintaining airway patency. The amplitude, frequency and duration of the mechanical stimulation are controlled such that sufficient stimulation of afferent nerves is achieved without sensory stimulation sufficient to cause arousal from sleep. The mechanical simulation of afferent nerves would typically be achieved by a period of several seconds of vibration at frequencies in the range of 10-50 Hz, and is tuned to the frequency at which the target receptors are most sensitive. The repetition rate of the stimulation is controlled according to the detected state of the airway.

For either electrical or mechanical stimulation, the level of stimulation depends on 2 factors: 1) sleep state; 2) state of upper airway. When the patient is awake, no treatment is delivered. When the patient is asleep, a baseline treatment is delivered which has the objective of increasing the background tone of the upper airway muscles such that it is similar to the tone during the awake state. This is designed to preemptively reduce the incidence of airway collapse. When the patient is asleep and airway obstruction is detected, treatment above the level of the baseline treatment is delivered which has the objective of restoring airway patency. Sleep state is determined by a combination of time of day and postural state, for example when the patient is supine and the time of day is coincident with the patient's normal sleeping time, sleep state is determined as asleep. Time of day is determined by a real time clock within the implanted device and postural state by a position sensor, also contained within the implanted device. When the sleep state is asleep, the baseline level of treatment is initiated. When the sleep state is asleep and obstruction is detected, the level of treatment is increased and maintained until such time as airway obstruction is no longer detected, as follows:

| | Sleep State/Airway State | | |
|---|---|---|---|
| | awake | asleep | Asleep plus airway obstruction |
| Treatment level | No treatment | Baseline treatment of 0-5 units | Incremental above baseline of 1-10 units |

An example of a methodology as described is illustrated in FIG. 1.

5.2 Detection of Respiratory Disorders Via Implanted Electrodes

5.2.1 Impedance

Implanted electrodes are ideally placed one either side of the thoracic cavity. eg one electrode is placed in the left sub pectoral region and a second electrode in the right sub pectoral region. One of these electrodes could be incorporated into the metallic case of an implanted device.

The transthoracic impedance is measured by emitting high frequency (eg 20 Hz) electrical pulses (compared with respiration or heart rate) that have amplitude and duration below the level needed to stimulate excitable tissue.

Typically current pulses of 1 mA amplitude and 15 micro second duration are emitted at a 20 Hz. This level of energy is well below the level required to stimulate excitable tissue.

The impedance changes are calculated by measuring current & voltage and calculating impedance via Ohm's Law. Impedance changes are correlated with thorax movements. Patterns of movement are detected and used to indicate a variety of respiratory disorders such as Obstructive Apnea, central apnea, Cheyne-Stokes respiration (CS-R).

To detect impedance changes the instantaneous transthoracic impedance signal is compared to a baseline reference. eg the baseline reference is a continuously updated average of the most recent 30 minutes of the transthoracic impedance signal.

The changes the transthoracic impedance signal are analysed in order to determine the state of respiration as follows:

| Respiration type | Transthoracic impedance |
|---|---|
| Normal respiration - no SDB | rhythmic variations at a rate of between 6 and 25 per minute; this rate averaged over; eg 2 minutes. Similarly an amplitude reference for 'normal breathing' is also derived; eg average amplitude of rhythmic variations over 30 minutes. |
| Obstructive | Marked reduction of amplitude as compared to the above reference; eg reduction of 30% or more; for at least 10 seconds. |
| Central apnea | first derivative of the impedance signal = essentially zero; no rhythmic variations for a period of 10 seconds or more |
| CSR | Derive the envelope of the rhythmic variations. Crescendo-decrescendo pattern denoted by a rhythmic variation in the envelope with a period of typically between 40 and 120 seconds or other classifier system. |

5.2.2 Impedance and Acoustic Transducers

A method for measuring airflow in an implantable device is by use of an acoustic transducer inside the device, such as a microphone, or from a transmitted signal from an external device in communication with the implantable device. Analysis of the frequency and amplitude of the sound can be used to deduce relative airflow. In addition, snoring, which is indicative of a partial obstruction of the upper airway can be detected. It is known that snoring is frequently a precursor of obstructive apnea.

A method for indicating thoracic movement is by measuring the electrical impedance between two or more implanted electrodes.

By a combination of methods for deducing airflow and thoracic movement, it is possible to discriminate between central and obstructive apnea in an implantable device. For example, if thoracic movements are detected without corresponding airflow, it is possible to deduce that there is obstructive apnea occurring. If there is no airflow and no thoracic movements for a specified period, it is possible to deduce that there is central apnea.

The invention claimed is:

1. A method for identifying a respiratory disorder in a patient using a device implanted in the patient, comprising:
    sensing patient sounds,
    analyzing frequency and amplitude of the patient sounds to determine airflow,
    measuring said patient's transthoracic impedance to determine thoracic movement, and
    identifying the respiratory disorder to distinguish central apnea and obstructive apnea based upon the determined airflow and determined thoracic movement;
    said device implanted in the patient including a microphone to sense patient sounds, a processor to analyze the frequency and amplitude of the sensed patient sounds to determine airflow, and an impedance detector to detect transthoracic impedance by 1) emitting high frequency electrical pulses to traverse the transthoracic cavity, and 2) calculating instantaneous transthoracic impedance across said transthoracic cavity.

2. The method of claim 1 wherein the impedance detector is configured to detect transthoracic impedance change by comparing said instantaneous transthoracic impedance to a recent average of instantaneous transthoracic impedances.

3. The method of claim 1 wherein said microphone further senses signals indicative of patient snoring which are used to determine the potential onset of sleep disordered breathing.

4. The method of claim 1 wherein the processor determines a potential onset of the respiratory disorder based on the patient sounds.

5. The method of claim 1 wherein transthoracic impedance is calculated by measuring current and voltage and by using Ohm's Law.

6. The method of claim 1 wherein said high frequency electrical pulses are at any energy level below the level required to stimulate excitable tissue.

7. The method of claim 1, wherein the processor determines occurrence of central apnea when there is no airflow and no thoracic movement.

8. The method of claim 1, wherein the processor determines occurrence of obstructive apnea when the thoracic movement is detected without corresponding airflow.

9. An implantable apparatus for determining the presence of sleep disordered breathing in a patient, comprising:
   an impedance detector configured to detect transthoracic impedance by 1) emitting high frequency electrical pulses to traverse the transthoracic cavity, and 2) calculating instantaneous transthoracic impedance across said transthoracic cavity,
   a microphone configured to capture signals representing patient sounds, and
   a processor configured to determine the presence of sleep disordered breathing;
   wherein said processor determines the presence of sleep disordered breathing by analyzing said patient-sound signals for frequency and amplitude to determine airflow, measuring said patient's transthoracic impedance to determine thoracic movement, determining the sleep disordered breathing to distinguish central apnea and obstructive apnea based upon the determined airflow and the patient's determined thoracic movement.

10. The apparatus of claim 9 wherein the impedance detector is configured to detect transthoracic impedance change by comparing said instantaneous transthoracic impedance to a recent average of instantaneous transthoracic impedances.

11. The apparatus of claim 9 wherein said microphone captures signals indicative of patient snoring which are used by said processor to identify the presence of sleep disordered breathing.

12. The apparatus of claim 9 wherein the processor determines thoracic movement by measuring electrical impedance between at least two electrodes.

13. The apparatus of claim 9 wherein transthoracic impedance is calculated by measuring current and voltage and by using Ohm's Law.

14. The apparatus of claim 9 wherein said high frequency electrical pulses are at an energy level below the level required to stimulate excitable tissue.

15. The apparatus of claim 9, wherein the processor determines occurrence of central apnea when there is no airflow and no thoracic movement.

16. The apparatus of claim 9, wherein the processor determines occurrence of obstructive apnea when the thoracic movement is detected without corresponding airflow.

17. A method for identifying a respiratory disorder in a patient using a device coupled to the patient, comprising:
   receiving signals associated with patient sounds,
   analyzing frequency and amplitude of the signals to determine airflow,
   measuring said patient's transthoracic impedance to determine thoracic movement, and
   determining the respiratory disorder to distinguish central apnea and obstructive apnea based upon the determined airflow and the determined thoracic movement;
   said device coupled to the patient including a microphone for receiving signals representative of patient sounds, a processor to determine airflow based on the frequency and amplitude of patient sounds, and an impedance detector to detect transthoracic impedance by 1) emitting high frequency electrical pulses to traverse the transthoracic cavity and 2) calculating instantaneous transthoracic impedance across said transthoracic cavity.

18. The method of claim 17 wherein the impedance detector is configured to detect transthoracic impedance change by comparing said instantaneous transthoracic impedance to a recent average of instantaneous transthoracic impedances.

19. The method of claim 17 wherein said microphone further receives signals indicative of patient snoring which are used to determine the potential onset of sleep disordered breathing.

20. The method of claim 17, wherein the processor determines the thoracic movement by measuring electrical impedance between at least two electrodes.

21. The method of claim 17 wherein the transthoracic impedance is calculated by measuring current and voltage and by using Ohm's Law.

22. The method of claim 17 wherein said high frequency electrical pulses are at an energy level below the level required to stimulate excitable tissue.

23. The method of claim 17, wherein the processor determines occurrence of central apnea when there is no airflow and no thoracic movement.

24. The method of claim 17, wherein the processor determines occurrence of obstructive apnea when the thoracic movement is detected without corresponding airflow.

25. An apparatus for determining sleep disordered breathing in a patient comprising:
   an impedance detector configured to detect transthoracic impedance by 1) emitting high frequency electrical pulses to traverse the transthoracic cavity, and 2) calculating instantaneous transthoracic impedance across said transthoracic cavity,
   a microphone configured to receive signals representing patient sounds, and
   a processor configured to process said signals to determine airflow based on frequency and amplitude of the patient sounds, the processor being configured to determine thoracic movement based on the transthoracic impedance;
   wherein said device is configured to determine the sleep disordered breathing to distinguish central apnea and obstructive apnea based upon the patient's determined thoracic movement and the determined airflow.

26. The apparatus of claim 25 wherein the impedance detector is configured to detect transthoracic impedance change by comparing said instantaneous transthoracic impedance to a recent average of instantaneous transthoracic impedances.

27. The apparatus of claim 25 wherein said microphone receives signals indicative of patient snoring which are used by said processor to identify the presence of sleep disordered breathing.

28. The apparatus of claim 25 wherein the processor determines the thoracic movement by measuring electrical impedance between at least two electrodes.

29. The apparatus of claim 25 wherein the transthoracic impedance is calculated by measuring current and voltage and by using Ohm's Law.

30. The apparatus of claim 25 wherein said high frequency electrical pulses are at an energy level below the level required to stimulate excitable tissue.

31. The apparatus of claim 25, wherein the processor determines occurrence of central apnea when there is no airflow and no thoracic movement.

32. The apparatus of claim 25, wherein the processor determines occurrence of obstructive apnea when the thoracic movement is detected without corresponding airflow.

* * * * *